United States Patent [19]

Helsley et al.

[11] Patent Number: 4,585,788
[45] Date of Patent: Apr. 29, 1986

[54] 6,11-DIHYDRODIBENZ[B,E]OXEPIN-ACETIC ACIDS AND DERIVATIVES

[75] Inventors: Grover C. Helsley, Pottersville; Arthur R. McFadden, East Brunswick, both of N.J.; David Hoffman, North Kingstown, R.I.

[73] Assignee: American Hoechst Corporation, Somerville, N.J.

[21] Appl. No.: 459,774

[22] Filed: Apr. 10, 1974

Related U.S. Application Data

[63] Continuation-in-part of Ser. No. 394,801, Sep. 6, 1973, abandoned.

[51] Int. Cl.[4] .................. C07D 313/12; A61K 31/335
[52] U.S. Cl. ...................... 514/450; 549/354
[58] Field of Search ............ 260/333; 549/354; 514/450

[56] References Cited

U.S. PATENT DOCUMENTS 3,702,852 11/1972 Yale et al. ............... 260/333
3,714,201 1/1973 Yale et al. ............... 260/333
3,758,528 9/1973 Malen et al. ............ 260/404

FOREIGN PATENT DOCUMENTS 48-389 6/1972 Japan .
000425 7/1972 Japan .

Primary Examiner—Norma S. Milestone
Attorney, Agent, or Firm—Curtis, Morris & Safford

[57] ABSTRACT 6,11-Dihydrodibenz[b,e]oxepin-acetic acids and derivatives having the general formula

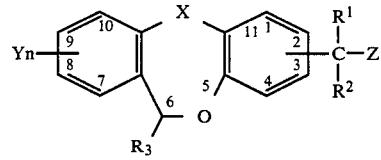

are prepared by multi-step sequences. X is C=O, CHCl, CHBr, $CH_2$ or $CHOR^4$; Y is alkyl or alkoxy of 1 to 4 carbon atoms, halogen or trifluoromethyl; n is 0, 1, 2 or 3; Z is $COOR^5$, $CH_2OR^5$, $CONR_2^5$ or $CONHOR^5$; and $R^1$-$R^5$ are hydrogen or alkyl of 1 to 4 carbon atoms.

These compounds and the physiologically tolerable salts thereof are useful as antiinflammatory and analgesic agents.

21 Claims, No Drawings

6,11-DIHYDRODIBENZ[B,E]OXEPIN-ACETIC ACIDS AND DERIVATIVES

This is a continuation in part of Application Ser. No. 394,801 filed Sept. 6, 1973, now abandoned.

This invention relates to 6,11-dihydrodibenz[b,e]oxepin-acetic acids and derivatives thereof having antiinflammatory and analgesic activity.

To the best of our knowledge, the compounds of this invention have not heretofore been described. Analogous sulfur compounds:

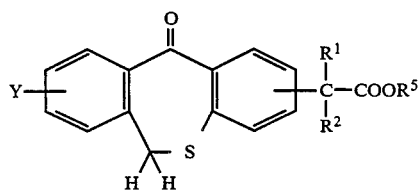

are mentioned in Japanese Patent Publication No. 72 00 425, published Jan. 7, 1972, as having analgesic, antipyretic and antiinflammatory activity.

The compounds of the invention have the formula:

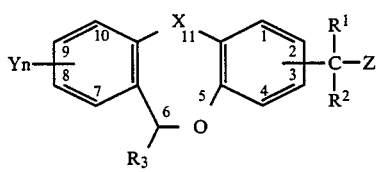

in which X is C=O, CHCl, CHBr, CH$_2$ or CHOR$^4$; Y is alkyl of 1 to 4 carbon atoms, alkoxy of 1 to 4 carbon atoms, halogen or trifluoromethyl; n is 0, 1, 2 or 3; Z is COOR$^5$, CH$_2$OR$^5$, CONHR$^5$, CONR$_2^5$, or CONHOR$^5$; and R$^1$ to R$^5$ are hydrogen or alkyl of 1 to 4 carbon atoms. The physiologically tolerable salts thereof are also included. A preferred compound is one in which R$^1$, R$^2$ and R$^3$ are hydrogen; X is C=O, Z is COOH; and n is 0.

Another preferred compound is the compound in which R$^1$ is CH$_3$; R$^2$ and R$^3$ are H; X is C=O, Z is COOH, and n is 0. Halogen is intended to mean F, Cl or Br.

Another very suitable compound of the invention is methyl 6,11-dihydro-11-oxodibenz[b,e]oxepin-2-acetate in which R$^1$, R$^2$ and R$^3$ are hydrogen, X is C=O, Z is COOCH$_3$, and n is zero. Still another important compound of the invention is 6, 11-dihydro-9-trifluoromethyl-11-oxodibenz[b,e]oxepin-2-acetic acid, in which R$^1$, R$^2$ and R$^3$ are H, X is C=O, Y is CF$_3$ in position 9, Z is COOH and n is 1.

The compounds of the present invention are prepared by a multi-step sequence of reactions as described below and illustrated in the attached flow sheet, in which Y, n, R$^1$, R$^2$ and R$^3$ are as defined earlier and R is alkyl.

A lower alkyl ester (I), i.e., an ester with 1 to 4 carbon atoms in the alcoholic unit, of a substituted α-bromotoluic acid is allowed to react with a lower alkyl ester of a hydroxyphenylacetic acid (II) which may be substituted in a solvent such as acetone, butanone, ethanol, or dimethylformamide with a base such as potassium carbonate or sodium hydride at a temperature of 0° C. to 120° C. for a time of 5 minutes to 12 hours to provide a diester of a substituted carboxybenzyloxyphenylacetic acid (III), which is then saponified with a base such as sodium or potassium hydroxide in a solvent such as ethanol or water for a time of from 15 minutes to 24 hours at a temperature 25° C. to 125° C. to provide a substituted carboxybenzyloxyphenylacetic acid (IV). This dicarboxylic acid is cyclized by treatment with a dehydrating medium such as polyphosphoric acid, ethanol phosphorus pentoxide, or sulfuric acid with or without a solvent such as tetramethylenesulfone or acetic acid at a temperature of 50° to 125° C. for a time of 15 minutes to 12 hours to provide a 6,11-dihydro-11-oxodibenz[b,e]oxepin-acetic acid (V).

A 6,11-dihydro-11-oxodibnez[b,e]oxepin-acetic acid (V) is allowed to react with an alcohol as methanol or ethanol in the presence of an acid, such as sulfuric, hydrochloric, or p-toluenesulfonic acid, at a temperature of 50° to 90° C. for a time of 15 minutes to 15 hours to provide a 6,11-dihydro-11-oxodibenz[b,e]oxepin-acetic acid ester (VI). This ester is reduced with sodium borohydride in a solvent, such as ethanol or 2-propanol, to a 6,11-dihydro-11-hydroxy-dibenz[b,e]oxepin-acetic acid ester (VII). The hydroxyester is converted to a bromoester with acetyl bromide or hydrobromic acid in a solvent such as benzene or toluene at a temperature of 35° to 120° C. for a time of 5 minutes to 2 hours to provide a 6,11-dihydro-11-bromo-dibenz[b,e]oxepin-acetic acid ester (VIII). This bromoester is reduced with sodium borohydride in a solvent such as diglyme (CH$_3$OCH$_2$CH$_2$OCH$_2$CH$_2$OCH$_3$) at a temperature of 25° to 80° C. for a time of 10 minutes to 3 hours to provide a 6,11-dihydro-dibenz[b,e]oxepin-acetic acid ester (IX), which is then saponified with a base such as sodium hydroxide for a time of 15 minutes to 24 hours at a temperature of 25° to 125° C. to provide a 6,11-dihydro-dibenz[b,e]oxepin-acetic acid (X).

A 6,11-dihydro-11-oxodibenz[b,e]oxepin-acetic acid (V) may also be allowed to react with thiony chloride or phosphorus oxychloride in a solvent such as chloroform, benzene, or dimethylformamide at a temperature of 25° to 85° for a time of 5 minutes to 4 hours to provide a substituted 6,11-dihydro-11-oxodibenz[b,e]oxepin-acetyl chloride (XI). This acid chloride is reacted with ammonia, alkylamine, or dialkylamine in a solvent such as chloroform, benzene, or ether at a temperature of 10° to 80° C. for a time of 10 minutes to 3 hours to provide a substituted 6,11-dihydro-11-oxodibenz[b,e]oxepin-acetamide (XII).

A 6,11-dihydro-11-oxodibenz[b,e]oxepin-acetic acid ester (VI) in which R$^1$ and R$^2$ are hydrogen may also be allowed to react with lithium aluminum hydride in a solvent such as ether or tetrahydrofuran at a temperature of 25° to 70° C. for a time of 10 minutes to 4 hours to provide a 6,11-dihydro-11-hydroxydibenz[b,e]oxepin-ethanol (XIII) or with sodium borohydride in an alcohol at a temperature of 10° to 70° C. for a time of 30 minutes to 12 hours to provide a 6,11-dihydro-11-alkoxydibenz[b,e]oxepin-acetic acid ester (XIV).

As well known to those skilled in the art, the reaction times are correlated to the reaction temperatures in the sense that shorter times are needed when using higher temperatures.

The compounds of the present invention are useful as antiinflammatory agents due to their ability to suppress inflammation in mammals. The activity of the compounds is demonstrated in the carrageenin induced rat paw edema antiinflammatory assay [Proc. Soc. Exptl. Biol. Med., III, 544 (1962); J. Pharmacol. Exp. Ther., 141, 369 (1963)]. For example, at doses of 6.5, 10, 17, and 25 mg/kg of body weight, 6,11-dihydro-11-oxodibenz[b,e]oxepin-2-acetic acid, 6,11-dihydro-α-methyl-11-oxodibenz[b,e]oxepin-2-acetic acid, methyl 6,11-dihydro-11-oxodibens[b,e]oxepin-2-acetate, and 8-chloro-6,11-dihydro-11-oxodibenz[b,e]oxepin-2-acetic acid, respectively, exhibit an approximately 50% inhibition of edema.

Compounds of the present invention are also useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. For example, at doses of 7.6 and 15.0 mg/kg of body weight, 6,11-dihydro-11-oxodibenz[b,e]oxepin-2-acetic acid and 6,11-dihydro-α-methyl-11-oxodibenz[b,e]oxepin-2-acetic acid, respectively, exhibit an approximately 50% inhibition of edema. These data illustrate that compounds of this invention are useful as antiinflammatory and analgesic agents at the dose of 0.1 to 50 mg/kg of body weight.

Examples of compounds of the invention are:
6,11-dihydro-α-propyl-11-oxodibenz[b,e]oxepin-2-acetic acid
6,11-dihydro-6-propyl-11-oxodibenz[b,e]oxepin-3-acetic acid
6,11-dihydro-9-chloro-11-oxodibenz[b,e]oxepin-2-acetic acid
6,11-dihydro-9-methoxy-11-oxodibenz[b,e]oxepin-3-acetic acid
6,11-dihydro-α,α-dipropyl-11-oxodibenz[b,e]oxepin-2-acetic acid t-butyl 6,11-dihydro-11-oxodibenz[b,e]oxepin-2-acetate
6,11-dihydro-11-t-butoxydibenz[b,e]oxepin-3-acetic acid
6,11-dihydro-9-ethyl-11-oxodibenz[b,e]oxepin-3-acetic acid
6,11-dihydro-10-fluoro-11-oxodibenz[b,e]oxepin-2-acetic acid
6,11-dihydro-11-ethyldibenz[b,e]oxepin-3-acetic acid
Especially interesting examples of compounds of the invention are: 6,11-dihydro-11-oxodibenz[b,e]oxepin-2-acetic acid and 6,11-dihydro-α-methyl-11-oxodibenz[b,e]oxepin-2-acetic acid.

The compounds of the present invention are valuable as pharmaceutical and veterinary products and may be administered to a patient by any convenient route such as orally, intramuscularly, intravenously, subcutaneously, or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% by weight of the unit. The amount of active compound in such compositions is such that a suitable dosage will be obtained. Preferred compositions and preparations according to the present invention are prepared so that an oral dosage unit form contains between 10 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or both. A syrup may contain, in addition to the active compounds sucrose as a sweetening agent, and certain preservatives, dyes and colorings, and flavors. Materials used in preparing these various compositions must be pharmaceutically pure and non-toxic in the amounts utilized.

EXAMPLE 1

6,11-Dihydro-11-oxodibenz[b,e]oxepin-2-acetic acid (a) A mixture of 100 g. of ethyl o-toluate, 100 g. of N-bromosuccinimide, and 0.3 g. of benzoyl peroxide in 1 liter of carbon tetrachloride is heated under reflux for 3 hours with stirring and filtered. The filtrate is washed with 3% aqueous sodium hydroxide and then with water, dried over magnesium sulfate, and concentrated under reduced pressure to provide ethyl α-bromo-o-toluate as an oil.

(b) A mixture of 20 g. of ethyl α-bromo-o-toluate, 14.4 g. of ethyl 4-hydroxyphenylacetate, 44 g. of potassium carbonate, 1.3 g. of potassium iodide and 200 ml. of 2-butanone is refluxed for sixteen hours. The salts are filtered and washed with ether and concentrated in vacuo to an oil. The oil is dissolved in ether and washed with sodium bicarbonate followed by water, dried over magnesium sulfate and evaporated to ethyl 4-(2-ethoxycarbonylbenzyloxy)phenylacetate as an oil.

(c) A mixture of 100 g of ethyl 4-(2-ethoxycarbonyl benzyloxy)phenylacetate, 100 g. of potassium hydroxide, and 1 liter of ethanol is refluxed with stirring for 3 hours. The mixture is concentrated in vacuo and the residue is dissolved in water. The solution is extracted with ether and the aqueous layer is acidified with hydrochloric acid. The precipitate is filtered and washed with hot ether to provide colorless crystals, m.p. 176°–178° C., of 4-(2-carboxybenzyloxy)phenylacetic acid.

(d) To 49 ml. of absolute ethanol is added with vigorous stirring, 81 g. of phosphorus pentoxide. After addition, the mixture is allowed to stir at 95°–100° C. for 1 hour, 400 ml. of tetramethylene sulfone are added, and the temperature is adjusted to 86°–90° C. Then, 38.5 g. of 4-(2-carboxybenzyloxy)phenylacetic acid are added, the mixture is stirred for 4 hours and poured onto ice water. The aqueous mixture is made basic with sodium hydroxide and extracted with toluene. Cooling of the aqueous layer followed by acidification with concentrated hydrochloric acid gives light brown crystals. Recrystallization from acetic acid-water or from dimethoxyethane provides colorless crystals, m.p. 126°–128° C. of 6,11-dihydro-11-oxodibenz[b,e]oxepin-2-acetic acid.

Analysis: Calculated for $C_{16}H_{12}O_4$: 71.64% C; 4.51% H. Found 71.44% C; 4.58% H.

Treatment of this acid with ethanolic potassium hydroxide provides the potassium salt, m.p. 214°–216° C.

Analysis: Calculated for $C_{16}H_{11}KO_4$: 62.73% C; 3.62% H. Found: 62.04% C; 3.45% H.

(e) As an alternative to step (d) above, 43.7 g. of polyphosphoric acid are added to 10.0 g. of 4-(2-carboxybenzyloxy)-phenylacetic acid in 35 ml. of glacial acetic acid. The mixture is vigorously stirred at 76° C. for 1⅜ hours and then hydrolyzed with 250 ml of water, the temperature being kept at 40° C. The precipitate which separates is collected and, when recrystallized from 2-propanol-water, provides pale yellow crystals, m.p. 137°–138°, of 6,11-dihydro-11-oxodibenz[b,e]oxepin-2-acetic acid.

Analysis: Calculated for $C_{16}H_{12}O_4$: 71.64% C; 4.51% H. Found: 71.58% C; 4.58% H.

EXAMPLE 2

6,11-Dihydro-α-methyl-11-oxodibenz[b,e]oxepin-2-acetic acid (a) Reaction of ethyl α-methyl-p-hydroxyphenylacetate with ethyl α-bromo-o-toluate by the method described in Example 1b provides ethyl 4-(2-ethoxycarbonylbenzloxy)-α-methylphenylacetate as a clear oil.

(b) Reaction of ethyl 4-(2-ethoxycarbonylbenzyloxy)-α-methylphenylacetate with potassium hydroxide by the method described in Example 1c provides colorless crystals, m.p. 145°–146° C., of 4-(2-carboxybenzyloxy)-α-methylphenylacetic acid.

(c) Reaction of 4-(2-carboxybenzyloxy)-α-methylphenylacetic acid with the phosphorus pentoxide-ethanol complex as previously described in Example 1d at a temperature of 96°–98° provides 6,11-dihydro-α-methyl-11-oxodibenz[b,e]oxepin-2-acetic acid as an oil; NMR: δ1.50 (d,3 protons, J=7.5 Hz), 3.73 (q, 1 proton, J=7.5 Hz), 5.12 (s, 2 protons) in $CDCL_3$.

EXAMPLE 3

6,11-Dihydro-α,α-dimethyl-11-oxodibenz[b,e]oxepin-2-acetic acid (a) Reaction of ethyl α,α-dimethyl-p-hydroxyphenylacetate with ethyl α-bromo-o-toluate as described in Example 1b provides ethyl 4-(2-ethoxycarbonylbenzloxy)-α,α-dimethylphenylacetate.

(b) Reaction of ethyl 4-(2-ethoxycarbonylbenzyloxy)-α,α-dimethylphenylacetate with potassium hydroxide as described in Example 1c provides 4-(2-carboxybenzyloxy)-α,α-dimethylphenylacetic acid.

(c) Reaction of 4-(2-carboxybenzyloxy)-α,α-dimethylphenylacetic acid with the phosphorus pentoxide-ethanol complex as described in Example 1d provides 6,11-dihydro-α,α-dimethyl-11-oxodibenz[b,e]oxepin-2-acetic acid.

EXAMPLE 4

Methyl 6,11-Dihydro-11-oxodibenz[b,e]oxepin-2-acetate

A mixture of 42 g. of 6,11-dihydro-11-oxodibenz[b,e]oxepin-2-acetic acid, 750 ml. of methanol, and 17 ml. of concentrated sulfuric acid is refluxed for 24 hours. The reaction mixture is diluted with water and extracted with benzene. After drying over magnesium sulfate, the benzene is concentrated to an oil. The precipitate resulting from addition of hexane is recrystallized from benzene-methanol to provide colorless crystals, m.p. 74°–76°, of methyl 6,11-dihydro-11-oxodibenz[b,e]oxepin-2-acetate.

Analysis: Calculated for $C_{17}H_{14}O_4$: 72.33% C; 5.00% H. Found: 72.47% C; 5.11% H.

EXAMPLE 5

6,11-Dihydro-6methyl-11-oxodibenz[b,e]oxepin-2-acetic acid (a) Reaction of ethyl o-ethylbenzoate with N-bromosuccinimide as described in Example 1a provides ethyl α-bromo-o-ethyl-benzoate as an oil.

(b) Reaction of ethyl α-bromo-o-ethylbenzoate with ethyl p-hydroxyphenylacetate as described in Example 1b provides ethyl 4-(2-ethoxycarbonyl-α-methylbenzyloxy)-phenylacetate as an oil.

(c) Reaction of ethyl 4-(2-ethoxycarbonyl-α-methylbenzyloxy)phenylacetate with potassium hydroxide as described in Example 1c provides colorless crystals, m.p. 171.5°–173.5°, of 4-(2-carboxy-α-methylbenzyloxy)phenylacetic acid.

(d) Reaction of 4-(2-carboxy-α-methylbenzyloxy)-phenylacetic acid with the phosphorus pentoxide-ethanol complex as described in Example 1d provides 6,11-dihydro-6-methyl-11-oxodibenz[b,e-]oxepin-2-acetic acid.

EXAMPLE 6

Methyl 6,11-Dihydro-11-methoxydibenz[b,e]oxepin-2-acetate

A mixture of 5.64 g. of methyl 6,11-dihydro-11-oxodibenz[b,e]oxepin-2-acetate, 0.4 g. of sodium borohydride and 250 ml. of methanol is stirred at 0°–2° for four hours. The reaction product is treated with 1 N hydrochloric acid and extracted with chloroform, and the chloroform extracts are washed with saturated sodium bicarbonate solution and dried with sodium sulfate. The chloroform is evaporated to leave methyl 6,11-dihydro-11-methoxydibenz[b,e]oxepin-2-acetate as an oil;

NMR: ($CDCl_3$) δ3.28 (s, 3 protons), 3.50 (s, 2 protons), 3.61 (s, 3 protons), 4.75 (d, 1 proton; J=12 Hz), 4.93 (s, 1 proton), 5.95 (d, 1 proton, J=12 Hz).

Analysis: Calculated for $C_{18}H_{18}O_4$: 72.47% C; 6.08% H. Found: 72.43% C; 6.16% H.

EXAMPLE 7

Isopropyl 6,11-Dihydro-11-hydroxydibenz[b,e]oxepin-2-acetate

A mixture of 1.25 g. of methyl 6,11-dihydro-11-oxodibenz[b,e]oxepin-2-acetate, 0.34 g. of sodium borohydride, 2 ml. of dimethylsulfoxide, and 25 ml. of isopropanol is stirred at room temperature for eighteen hours. The reaction mixture is dissolved in 500 ml. of water and acidified with 1N hydrochloric acid at 5°. The acidic solution is extracted with chloroform, and the chloroform solution is washed with a saturated sodium bicarbonate solution and dried over sodium sulfate. Concentration in vacuo provides isopropyl 6,11-dihydro-11-hydroxydibenz[b,e]-oxepin-2-acetate as an oil;

NMR: ($CDCl_3$) δ1.18 (d, 6 protons, J=6 Hz), 3.43 (broad, 1 proton), 4.85 (d, 1 proton, J=12 Hz), 4.90 (septet, 1 proton, J=6 Hz), 5.50 (broad, 1 proton), 5.75 (d, 1 proton, J=12 Hz).

EXAMPLE 8

Methyl 6,11-Dihydro-11-hydroxydibenz[b,e]oxepin-2-acetate

A solution of 1.4 g. of sodium borohydride, 200 ml. of methanol, and 4.0 g. of methyl 6,11-dihydro-11-oxodibenz[b,e]oxepin-2-acetate is stirred at 5°–10° for four hours and then the methanol is removed under high vacuum. Water and tetrahydrofuran are added to the residue, and the solution is adjusted to a pH of 5–6 with the addition of acetic acid and stirred for two hours at room temperature. The mixture is extracted with chloroform, and the chloroform solution is dried over sodium sulfate and concentrated. Trituration of the solid with ether provides methyl 6,11-dihydro-11-hydroxydibenz[b,e]oxepin-2-acetate as colorless crystals, m.p. 85°–87°.

Analysis: Calculated for $C_{17}H_{16}O_4$: 71.81% C; 5.67% H. Found: 71.78% C; 5.75% H.

EXAMPLE 9

6,11-Dihydrodibenz[b,e]oxepin-2-acetic acid (a) A mixture of 5.7 g. of methyl 6,11-dihydro-11-hydroxybenz[b,e](oxepin-2-acetate, 5 ml. of acetyl bromide and 60 ml. of dry benzene is refluxed for two hours. Evaporation in vacuo provides methyl 6,11-dihydro-11-bromodibenz[b,e]oxepin-2-acetate as a yellow oil.

NMR: $\delta$3.55 (s, 2 protons), 3.68 (s, 3 protons), 4.98 (d, 1 proton, J=13.5 Hz), 6.28 (d, 1 proton, J=13.5 Hz), 6.42 (s, 1 proton) in $CDCl_3$.

(b) A mixture of 6.0 g. of sodium borohydride, 26 ml. of diglyme, 14 ml. of water, and 4.8 g. of methyl 6,11-dihydro-11-bromodibenz[b,e]oxepin-2-acetate is heated at 50° for one hour. Water is added and the mixture is extracted with ether. The ether extracts are dried with sodium sulfate, filtered, and concentrated in vacuo to provide methyl 6,11-dihydrodibenz[b,e]oxepin-2-acetate.

(c) Reaction of methyl 6,11-dihydrodibenz[b,e]oxepin-2-acetate and potassium hydroxide in ethanol by the method described in Example 1c provides 6,11-dihydrodibenz[b,e]oxepin-2-acetic acid, m.p. 155°–157°.

Analysis: Calculated for $C_{16}H_{14}O_3$: 75.57% C; 5.55% H.
Found: 75.48% C; 5.51% H.

EXAMPLE 10

6,11-Dihydro-11-oxodibenz[b,e]oxepin-2-acetamide (a) A mixture of 5.4 g. of 6,11-dihydro-11-oxodibenz[b,e]oxepin-2-acetic acid, 2.4 g. of thionyl chloride, 10 ml. of chloroform and 1 ml. of dimethylformamide is heated for one hour under reflux. The excess thionyl chloride is distilled under reduced pressure.

The above acid chloride is dissolved in chloroform and the solution saturated with ammonia. The precipitate is filtered and the chloroform is concentrated to an oil. Recrystallization from acetonitrile provides white crystals, m.p. 157°–158°, of 6,11-dihydro-11-oxodibenz[b,e]oxepin-2-acetamide.

Analysis: Calculated for $C_{16}H_{13}NO_3$: 71.90% C; 4.90% H. Found: 71.89% C; 4.83% H.

EXAMPLE 11

6,11-Dihydro-N-methyl-11-oxodibenz[b,e]oxepin-2-acetamide

Reaction of 6,11-dihydo-11-oxodibenz[b,e]oxepin-2-acetylchloride and methylamine by the method of Example 10 provides 6,11-dihydro-N-methyl-11-oxodibenz[b,e]oxepin-2-acetamide.

EXAMPLE 12

6,11-Dihydro-N,N-dimethyl-11-oxodibenz[b,e]oxepin-2-acetamide

Reaction of 6,11-dihydro-11-oxodibenz[b,e]oxepin-2-acetylchloride and dimethylamine by the method described in Example 11, provides 6,11-dihydro-N,N-dimethyl-11-oxodibenz[b,e]oxepin-2-acetamide.

EXAMPLE 13

6,11-Dihydro-8-fluoro-11-oxodibenz[b,e]oxepin-2-acetic acid (a) Reaction of ethyl 4-fluoro-o-toluate with N-bromosuccinimide as described in Example 1a provides ethyl α-bromo-4-fluoro-o-toluate.

(b) Reaction of ethyl α-bromo-4-fluoro-o-toluate with ethyl p-hydroxyphenylacetate as described in Example 1b provides ethyl 4-(2-ethoxycarbonyl-5-fluorobenzyloxy)phenylacetate.

(c) Reaction of ethyl 4-(2-ethoxycarbonyl-5-fluorobenzyloxy)phenylacetate with potassium hydroxide as described in Example 1c provides 4-(2-carboxy-5-fluorobenzyloxy)phenylacetic acid.

(d) Reaction of 4-(2-carboxy-5-fluorobenzyloxy)phenylacetic acid with the phosphorus pentoxide-ethanol complex as previously described in Example 1d provides 6,11-dihydro-8-fluoro-11-oxodibenz[b,e]oxepin-2-acetic acid.

EXAMPLE 14

6,11-Dihydro-8-chloro-11-oxodibenz[b,e]oxepin-2-acetic acid (a) Reaction of ethyl 4-chloro-o-toluate with N-bromosuccinimide as described in Example 1a provides ethyl α-4-chloro-o-toluate as an oil.

(b) Reaction of ethyl α-bromo-4-chloro-o-toluate with ethyl p-hydroxyphenylaceta in Example 1b provides ethyl 4-(2-ethoxycarbonyl-5-chlorobenzyloxy)-phenylacetate as a yellow oil.

(c) Reaction of ethyl 4-(2-ethoxycarbonyl-5-chlorobenzyloxy)phenylacetate with potassium hydroxide as described in Example 1c provides 4-(2-carboxy-5-chlorobenzyloxy)phenylacetic acid as a colorless solid, m.p. 197°–201°.

(d) Reaction of 4-(2-carboxy-5-chlorobenzyloxy)-phenylacetic acid with the phosphorus pentoxide-ethanol complex as described in Example 1d at a temperature of 85°–90° C. provides 6,11-dihydro-8-chloro-11-oxodibenz[b,e]oxepin-2-acetic acid as colorless crystals, m.p. 188°–190° C.

Analysis: Calculated for $C_{16}H_{11}ClO_4$: 63.48% C; 3.66% H. Found: 63.28% C; 3.67% H.

EXAMPLE 15

6,11-Dihydro-9-chloro-11-oxodibenz[b,e]oxepin-2-acetic acid (a) Reaction of ethyl 5-chloro-o-toluate with N-bromosuccinimide as described in Example 1a provides ethyl α-bromo-5-chloro-o-toluate.

(b) Reaction of ethyl α-bromo-5-chloro-o-toluate with ethyl p-hydroxyphenylacetate described in Example 1b provides ethyl 4-(2-ethoxycarbonyl-4-chlorobenzyloxy)phenylacetate.

(c) Reaction of ethyl 4-(2-ethoxycarbonyl-4-chlorobenzyloxy)phenylacetate with potassium hydroxide as described in Example 1c provides 4-(2-carboxy-4-chlorobenzyloxy)phenylacetic acid, m.p. 205°–208°.

(d) Reaction of 4-(2-carboxy-4-chlorobenzyloxy)-phenylacetic acid with the phosphorus pentoxide-ethanol complex as described in Example 1d provides 6,11-dihydro-9-chloro-11-oxodibenz[b,e]oxepin-2-acetic acid, m.p. 169°–171°.

Analysis: Calculated for $C_{16}H_{11}ClO_4$: 63.48% C; 3.66% H; 11.71% Cl.
Found: 63.20% C; 3.79% H; 11.51% Cl.

EXAMPLE 16

6,11-Dihydro-9-trifluoromethyl-11-oxodibenz[b,e]oxepin-2-acetic acid (a) Reaction of ethyl 5-trifluoromethyl-o-toluate with N-bromosuccinimide as described in Example 1a provides ethyl α-bromo-5-trifluoromethyl-o-toluate.

(b) Reaction of ethyl α-bromo-5-trifluoromethyl-o-toluate with ethyl p-hydroxyphenylacetate as described in Example 1b provides ethyl 4-(2-ethoxycacrbonyl-4-trifluoromethylbenzyloxy)phenylacetate.

(c) Reaction of ethyl 4-(2-ethoxycarbonyl-4-trifluoromethylbenzyloxy)phenylacetate with potassium hydroxide as described in Example 1c provides 4-(2-carboxy-4-trifluoromethylbenzyloxy)phenylacetic acid, m.p. 185°–187°.

(d) Reaction of 4-(2-carboxy-4-trifluoromethylbenzyloxy)phenylacetic acid with the phosphorus pentoxide-ethanol complex as described in Example 1d provides 6,11-dihydro-9-trifluoromethyl-11-oxodibenz[b,e]oxepin-2-acetic acid, m.p. 152°–155°.

Analysis: Calculated for $C_{17}H_{11}F_3O_4$: 60.72% C; 3.30% H. Found: 60.68% C; 3.38% H.

EXAMPLE 17

6,11-Dihydro-8-methoxy-11-oxodibenz[b,e]oxepin-2-acetic acid (a) Reaction of ethyl 4-methoxy-o-toluate with N-bromosuccinimide as described in Example 1a provides ethyl α-bromo-4-methoxy-o-toluate as a colorless liquid.

(b) Reaction of ethyl α-bromo-4-methoxy-o-toluate with ethyl p-hydroxyphenylacetate as described in Example 1b provides ethyl 4-(2-ethoxycarbonyl-5-methoxybenzyloxy)phenylacetate as a yellow oil.

(c) Reaction of 4-(2-ethoxycarbonyl-5-methoxybenzyloxy) phenylacetate with potassium hydroxide as described in Example 1c provides 4-(2-carboxy-5-methoxybenzyloxy)phenylacetic acid as colorless crystals, m.p. 198°–200° C.

(d) Reaction of 4-(2-carboxy-5-methoxybenzyloxy)-phenylacid with the phosphorus pentoxide-ethanol complex as described in Example 1d at a temperature of 85°–88° C. provides 6,11-dihydro-8-methoxy-11-oxodibenz[b,e]oxepin-2-acetic acid as a colorless solid, m.p. 163°–165° C.

Analysis: Calculated for $C_{17}H_{14}O_5$: 68.45% C; 4.73% H. Found: 68.37% C; 4.94% H.

EXAMPLE 18

6,11-Dihydro-11-hydroxydibenz[b,e]oxepin-2-ethanol

A solution of 3.5 g. of methyl 6,11-dihydro-11oxodibenz[b,e]oxepin-2-acetate in 150 ml. of dry ether is added dropwise to suspension of 2.5 g. of lithium aluminum hydride in 50 ml. of dry ether. The mixture is refluxed for three hours, cooled to 0° C., and hydrolyzed. The mixture is extracted with ether, dried over sodium sulfate, and evaporated to a crude crystalline product. Recrystallization from acetonitrile provides colorless crystals, m.p. 135°–137° C. of 6,11-dihydro-11-hydroxydibenz-[b,e]oxepin-2-ethanol.

Analysis: Calculated for $C_{16}H_{16}O_3$: 74.98% C; 6.29% H. Found: 75.10% C; 6.35% H.

EXAMPLE 19

6,11-Dihydro-11-hydroxydibenz[b,e]oxepin-2-acetic acid

A solution of 5.0 g. of 6,11-dihydro-11-oxodibenz[b,e]oxepin-2-acetic acid in 16 ml. of 5% sodium hydroxide is added dropwise to a cold solution of 1.36 g. of sodium borohydride in 40 ml. of water. The reaction mixture is stirred at 0° C. for 4 hours, poured onto ice, and acidified with glacial acetic acid. The precipitate is filtered and washed with water to provide colorless crystals, m.p. 132°–133.5° C. of 6,11-dihydro-11-hydroxydibenz[b,e]oxepin-2-acetic acid.

Analysis: Calculated for $C_{16}H_{14}O_4$: 71.10% C; 5.22% H. Found: 71.25% C; 5.21% H.

EXAMPLE 20

6,11-Dihydro-9-fluoro-11-oxodibenz[b,e]oxepin-2-acetic acid (a) Reaction of ethyl 5-fluoro-o-toluate with N-bromosuccinimide as described in Example 1a provides ethyl α-bromo-5-fluoro-o-toluate as an oil.

(b) Reaction of ethyl α-bromo-5-fluoro-o-toluate with ethyl p-hydroxyphenylacetate as described in Example 1b provides ethyl 4-(2-ethoxycarbonyl-4-fluorobenzyloxy)phenylacetate as an oil.

(c) Reaction of ethyl 4-(2-ethoxycarbonyl-4-fluorobenzyloxy)phenylacetate with potassium hydroxide as described in Example 1c provides colorless crystals, m.p. 195°–197° C. of 4-(2-carboxy-4-fluoro-benzyloxy)phenylacetic acid.

(d) Reaction of 4-(2-carboxy-4-fluorobenzyloxy)-phenylacetic acid with the phosphorus pentoxide-ethanol complex as previously described in Example 1d provides beige crystals, m.p. 173°–175° C., of 6,11-dihydro-9-fluoro-11-oxodibenz[b,e]oxepin-2-acetic acid.

Analysis: Calculated for $C_{16}H_{11}FO_4$: 67.13% C; 3.87% H; 6.64% F. Found: 67.05% C; 4.04% H; 6.46% F.

EXAMPLE 21

6,11-Dihydro-7-chloro-11-oxodibenz[b,e]oxepin-2-acetic acid (a) Reaction of ethyl 3-chloro-o-toluate with N-bromosuccinimide as described in Example 1a provides ethyl α-bromo-3chloro-o-toluate as an oil.

(b) Reaction of ethyl α-bromo-3-chloro-o-toluate with ethyl p-hydroxyphenylacetate as described in Example 1b provides ethyl 4-(2-chloro-6-ethoxycarbonylbenzyloxy)phenylacetate as an oil.

(c) Reaction of ethyl 4-(2-chloro-6-ethoxycarbonylbenzyloxy)phenylacetate with potassium hydroxide as described in Example 1c provides 4-(2-carboxy-6-chlorobenzyloxy)phenylacetic acid as a colorless solid, m.p. 171°–173° C.

(d) Reaction of 4-(2-carboxy-6-chlorobenzyloxy)phenylacetic acid with the phosphorus pentoxide-ethanol complex as described in Example 1d at a temperature of 86° C. provides 6,11-dihydro-7-chloro-11-oxodibenz[b,e]oxepin-2-acetic acid as beige crystals, m.p. 173°–176° C.

Analysis: Calculated for $C_{16}H_{11}ClO_4$: 63.48% C; 3.66% H. Found: 62.93% C; 3.64% H.

EXAMPLE 22

Isopropyl 6,11-Dihydro-11-oxodibenz[b,e]oxepin-2-acetate

Reaction of 6,11-dihydro-11-oxodibenz[b,e]oxepin-2-acetic acid with 2-propanol as described in Example 4 provides isopropyl 6,11-dihydro-11-oxodibenz[b,e]oxepin-2-acetate as colorless crystals, m.p. 67°–68.5° C.

Analysis: Calculated for $C_{19}H_{18}O_4$: 73.53% C; 5.85% H. Found: 73.59% C; 5.92% H.

EXAMPLE 23

6,11-Dihydro-10-methyl-11-oxodibenz[b,e]oxepin-2-acetic acid (a) Reaction of methyl 2,6-dimethylbenzoate with N-bromosuccinimide as described in Example 1a provides methyl 2-bromomethyl-6-methylbenzoate as an oil.

(b) Reaction of methyl 2-bromoethyl-6-methylbenzoate with ethyl p-hydroxyphenylacetate as described in Example 1b provides ethyl 4-(3-methyl-2-methoxycarbonylbenzloxy)phenylacetate as an oil.

(c) Reaction of ethyl 4-(3-methyl-2-methoxycarbonylbenzyloxy)phenylacetate with potassium hydroxide as described in Example 1c provides beige crystals, m.p. 168°–170°, of 4-(2-carboxy3-methylbenzyloxy)phenylacetic acid.

(d) Reaction of 4-(2-carboxy-3-methylbenzyloxy)phenylacetic acid with the phosphorus pentoxide-ethanol complex as described in Example 1d provides 6,11-dihydro-10-methyl-11-oxodibenz[b,e]oxepin-2-acetic acid, m.p. 183°–185°.

I claim:

1. A compound of the formula

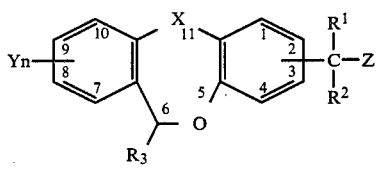

in which X is C=O, CHCl, CHBr, $CH_2$ or $CHOR^4$; Y is alkyl or alkoxy of 1 to 4 carbon atoms, F, Cl, Br or trifluoromethyl; n is 0 or 1; Z is $COOR^5$, $CH_2OR^5$, $CONHR^5$, $CONR_2^5$ or $CONHOR^5$; and $R^1$, $R_2$, $R^3$, $R^4$ and $R^5$ are hydrogen or alkyl of 1 to 4 carbon atoms; and the physiologically tolerable salts thereof.

2. A compound as defined in claim 1 in which X is C=O, $CH_2$, CHOH or $CHOCH_3$; Y is methyl, methoxy, F, Cl or $CF_3$; n is 0 or 1; Z is COOH, $COOCH_3$, $COOC_3H_7$, $CH_2OH$, $CONH_2$, $CONCH_3$ or $CON(CH_3)_2$ and $R^1$, $R^2$ and $R^3$ are hydrogen or methyl.

3. The compound, as claimed in claim 1, wherein the

moiety is substituted in the 2- or 3-position of the tricyclic nucleus, n is 0 or 1 and with the proviso that Z is not $CH_2OR^5$ when X is C=O, CHCl, CHBr or $CH_2$.

4. A compound of the formula

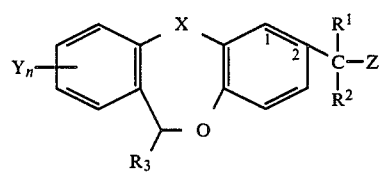

in which X is C=O, CHCl, CHBr, $CH_2$ or CHOH; Y is alkyl or alkoxy of 1 to 4 carbon atoms, F, Cl, Br or trifluoromethyl; n is 0 or 1; Z is $COOR^5$, $CH_2OH$, $CONHR^5$, $CONR_2^5$ or $CONHOR^5$, with the proviso that Z is not $CH_2OH$ when X is C=O, CHCl, CHBr or $CH_2$; $R_1$, $R_2$, $R_3$, $R_4$ and $R_5$ are hydrogen or alkyl of 1 to 4 carbon atoms; and the physiologically tolerable salts thereof.

5. The compound defined in claim 1 which is 6,11-dihydro-6-propy-11-oxodibenz[b,e]oxepin-3-acetic acid.

6. A method of treating inflammation and pain which comprises administering to a patient an effective amount of the compound defined in claim 1.

7. An orally administrable composition for treating inflammation and pain in a mammal which consists essentially of a pharmaceutically acceptable carrier and from about 1 to about 200 mg. of a compound as defined in claim 1.

8. A compound of the formula

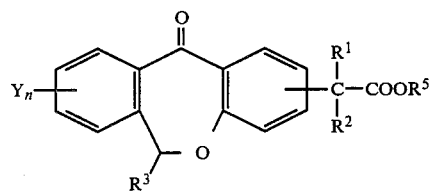

in which Y is alkyl or alkoxy of 1 to 4 carbon atoms, F, Cl, Br or $CF_3$; n is 0 or 1; $R^1$, $R^2$, $R^3$ and $R^5$ are hydrogen or alkyl of 1 to 4 carbon atoms the

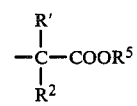

moiety being substituted in the 2- or 3-position of the tricyclic nucleus; and the physiologically tolerable salts thereof.

9. A compound of the formula

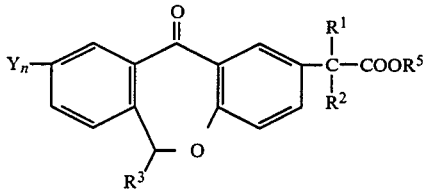

in which Y, n, $R^1$, $R^2$, $R^3$ and $R^5$ are as defined in claim 8.

10. The compound defined in claim 8 which is 6,11-dihydro-11-oxodibenz[b,e]oxepin-2-acetic acid.

11. The compound defined in claim 8 which is 6,11-dihydro-α-methyl-11-oxodibenz[b,e]oxepin-2-acetic acid.

12. The compound defined in claim 8 which is methyl 6,11-dihydro-11-oxodibenz[b,e]oxepin-2-acetate.

13. The compound defined in claim 8 which is 6,11-dihydro-8-chloro-11-oxodibenz[b,e]oxepin-2-acetic acid.

14. The compound defined in claim 8 which is 6,11-dihydro-8-methoxy-11-oxodibenz[b,e]oxepin-2-acetic acid.

15. The compound defined in claim 8 which is 6,11-dihydro-9-fluoro-11-oxodibenz[b,e]oxepin-2-acetic acid.

16. A compound of the formula

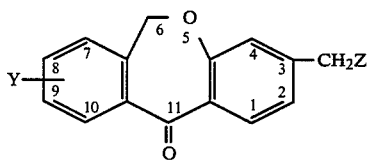

in which Z is a carboxyl or lower alkoxycarbonyl group and Y is a lower alkyl or lower group of 1–4 carbon atoms; and the pharmaceutically acceptable salts thereof.

17. The compound defined in claim 16 which is 6,11-dihydro-9-methoxy-11-oxodibenz[b,e]oxepin-3-acetic acid.

18. The compound defined in claim 16, which is 6,11-dihydro-9-ethyl-11-oxodibenz[b,e]oxepin-3-acetic acid.

19. A compound of the formula

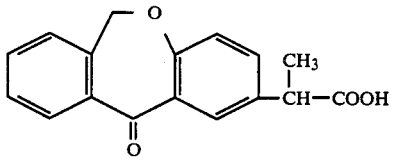

and the pharmaceutically acceptable salts thereof.

20. A compound of the formula

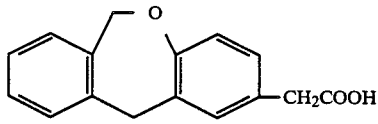

and the pharmaceutically acceptable salts thereof.

21. A compound of the formula

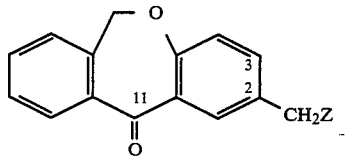

wherein Z is a carboxyl or lower alkoxycarbonyl group and the pharmaceutically acceptable salts thereof.

* * * * *